United States Patent [19]

Kraus

[11] Patent Number: 5,480,995
[45] Date of Patent: Jan. 2, 1996

[54] PROCESS FOR THE PREPARATION OF 6-AMINO-NICOTINONITRILES

[75] Inventor: Helmut Kraus, Köln, Germany

[73] Assignee: Bayer Aktiengesellschaft, Leverkusen, Germany

[21] Appl. No.: 179,786

[22] Filed: Jan. 11, 1994

[30] Foreign Application Priority Data

Jan. 18, 1993 [DE] Germany ............... 43 01 109.8

[51] Int. Cl.$^6$ ............ C07D 213/09; C07D 213/85; C07D 401/02; C07D 413/02
[52] U.S. Cl. ............ 546/250; 546/193; 546/289; 544/124; 544/360
[58] Field of Search ............... 546/250, 289, 546/193; 544/124, 360

[56] References Cited

U.S. PATENT DOCUMENTS

| | | | |
|---|---|---|---|
| 4,405,552 | 9/1983 | Miesel | 514/348 |
| 4,849,432 | 7/1989 | Shiokawa et al. | 514/341 |

FOREIGN PATENT DOCUMENTS

| | | | |
|---|---|---|---|
| 0060071 | 9/1982 | European Pat. Off. | 514/353 |
| 0181636 | 5/1986 | European Pat. Off. | 514/344 |
| 0235725 | 9/1987 | European Pat. Off. | 546/250 |
| 0383091 | 8/1990 | European Pat. Off. | 546/331 |
| 3726993 | 2/1989 | Germany | 546/329 |
| 1215387 | 12/1970 | United Kingdom | 546/345 |

OTHER PUBLICATIONS

F. Scotti et al., *J. Org. Chem.*, 29, 1800 (1964).
Science, Oct. 3, 1969, vol. 166, No. 3901; "Photochemical reactions and the chemical evolution of purines and nicotinamide derivatives", J. P. Ferris et al; cover page and pp. 765–766.
(Abstract) [JP] Japanese Patent 099595 pub. Nov. 15, 1986.
The Chemistry of Heterocyclic Compounds, Part 5, pp. 118–141, 227–231, (1979).
J. Chem. Soc. pp. 5542–5551 (1965).

*Primary Examiner*—Alan L. Rotman
*Attorney, Agent, or Firm*—Sprung Horn Kramer & Woods

[57] ABSTRACT

6-Amino-nicotinonitriles of the formula

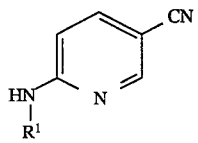 (I)

can be prepared by reacting methylene-glutacononitriles of the formula

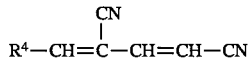 (II)

with nitrogen compounds of the formula $R^1$—$NH_2$   (III)

at 0° to 200° C. in the presence or absence of an inert solvent. The ratio of nitrogen compound to glutacononitrile is 1 to 100:1. The substituents $R^1$ and $R^4$ have the meanings given in the description.

13 Claims, No Drawings

PROCESS FOR THE PREPARATION OF 6-AMINO-NICOTINONITRILES

The invention relates to a process for the preparation of 6-amino-nicotinonitriles (2-amino-5-cyano-pyridines) via the intermediate of the 2-imino-5-cyano-1,2-dihydro-pyridines by reacting methylene-glutacononitriles with primary amines, hydrazines or ammonia.

The heterocycles which can be prepared according to the invention are intermediates for the preparation of pharmaceutical and agrochemical active compounds (EP 181,636, JP 61/257 960 (1986)). Since 2-amino-pyridines can be reacted readily to give the corresponding halogen compounds (GB 1,215,387), 6-amino-nicotinonitrile is an important intermediate for the synthesis of insecticides from the nitromethylene class (EP 235,725, EP 383,091, German Offenlegungsschrift 3,726,993).

2-Amino-pyridines can be prepared from the suitably substituted starting substances by the method of Tschitschibabin using sodium amides in liquid ammonia. In most cases, however, this method has the problem that undesired isomers are formed. A specific synthesis by subjecting suitable nitriles with amines to a cyclization reaction is possible in good yields in the case of some substituted pyridines (The Chemistry of Heterocyclic Compounds (G. R. New Kome), Interscience/John Wiley, Part 5, Pyridine, p. 118). Furthermore, 2-amino-5-phenyl-pyridine can be prepared starting from 4-dimethylamino-3-phenyl-1,3-pentadienonitrile with ammonia in dimethyl sulphoxide (EP 60,071); however, only 300 mg of the desired product are obtained from 3 g of starting material.

6-Amino-nicotinonitrile is accessible in a yield of 10% by exposing 2-formyl-glutacononitrile in 1-molar ammoniacal solution to light (Science 166, 765), while a purely thermal synthesis is only possible in even lower yields (J. Mol. Biol. 33 (1968), 693, as cited in Science, loc. cit.).

5-Cyano-1,2-dihydro-2-imino-1-methylpyridine can be prepared starting from 2-amino-5-cyanopyridine by methylating it with methyl iodide and subsequently liberating the product using alkali (J. Chem. Soc. 1965, 5542).

Taking into consideration this prior art, it is surprising that methylene-glutacononitriles can be reacted in high yield to give the corresponding 2,5-disubstituted pyridines.

Accordingly, the invention relates to a process for the preparation of 6-amino-nicotinonitriles of the formula

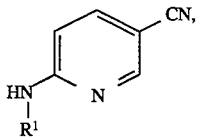 (I)

in which
R$^1$ denotes hydrogen, straight-chain or branched C$_1$–C$_8$-alkyl, C$_3$–C$_8$-alkenyl, C$_2$–C$_8$-alkoxyalkyl, C$_4$–C$_8$-alkoxyalkenyl, C$_3$–C$_8$-cycloalkyl, C$_7$–C$_{10}$-aralkyl or —N(R$^2$R$^3$), where R$^2$ and R$^3$ independently of one another denote hydrogen, straight-chain or branched C$_1$–C$_8$-alkyl, phenyl, tolyl, C$_7$–C$_{10}$-aralkyl or a 5- to 8-membered saturated or unsaturated heterocyclic ring having 1 or 2 hetero atoms from the group consisting of N, O and S, where furthermore R$^2$ and R$^3$ together with the N atom to which they are bonded can form a 5- to 8-membered ring which can contain a further hetero atom from the group consisting of N, O and S, which is characterized in that methylene-glutacononitriles of the formula

in which
R$^4$ represents —OR$^5$ or —N(R$^5$, R$^6$)
where R$^5$ and R$^6$ independently of R$^1$ and independently of one another have the scope of meaning of R$^1$ with the exception of hydrogen, where furthermore R$^5$ and R$^6$ together with the N atom to which they are bonded can form a 5- to 8-membered ring which can contain a further hetero atom from the group consisting of N, O and S, are reacted with nitrogen compounds of the formula $$R^1—NH_2 \quad (III)$$

in which
R$^1$ has the abovementioned meaning,
at a temperature from 0° to 200° C., preferably 20° to 150° C., and a molar ratio of nitrogen compound to glutacononitrile of 1 to 100:1, preferably 1 to 10:1, and in the presence or absence of an inert solvent.

In accordance with the meanings of R$^1$, the glutacononitrile is therefore reacted with ammonia, a primary amine or a hydrazine.

Straight-chain or branched C$_1$–C$_8$-alkyl is, for example, methyl, ethyl, propyl, isopropyl, butyl, isobutyl, tert.-butyl, and the amyl, hexyl and octyl isomers, preferably the abovementioned C$_1$–C$_4$-alkyl radicals.

C$_3$–C$_8$-Alkenyl is allyl or the butenyl, amylenyl, hexenyl or octenyl isomers, preferably the abovementioned C$_3$–C$_4$-alkenyl radicals.

C$_2$–C$_8$-Alkoxyalkyl is, for example, methoxymethyl, ethoxymethyl, methoxyethyl and other radicals from the C$_3$–C$_9$-alkyl group in which a CH$_2$ group is replaced by an O atom.

C$_4$–C$_8$-Alkoxyalkenyl is, for example, methoxyallyl, 2-methoxy-propenyl and other radicals from the C$_4$–C$_9$-alkenyl group in which a CH$_2$ group is replaced by an O atom.

C$_3$–C$_8$-Cycloalkyl is, for example, cyclopropyl, methylcyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl, cyclooctyl, preferably cyclopropyl, cyclopentyl and cyclohexyl, and their methyl or dimethyl derivatives.

C$_7$–C$_{10}$-aralkyl is, for example, benzyl, 1-phenylethyl, 2-phenylethyl and other radicals of this type known to those skilled in the art, preferably benzyl.

The following may be mentioned as 5- to 8-membered, saturated or unsaturated heterocyclic ring whose hetero atoms 1 and 2 are selected from the group consisting of N, O and S: pyrrole, furan, thiophene, pyrrolidine, pyrazole, imidazole, thiazole, oxazole, pyridine, pyrimidine, piperazine, morpholine, pyran, azepine, azocine, isoxazole, isothiazole, pyridazine and pyrazine. It is known to those skilled in the art that unsaturated heterocyclic rings can have a more or less pronounced aromatic character.

Furthermore, R$^2$ and R$^3$ together with the N atom to which they are bonded can form a 5- to 8-membered ring which can contain a further hetero atom selected from the group consisting of N, O and S. Such systems are, for example, pyrrolidine, pyrroline, pyrazolidine, imidazolidine, thiazolidine, piperazine, piperidine, morpholine, azepine or dihydroazocine.

In a preferred manner, the process according to the invention employs methylene-glutacononitriles in which $R^2$ and $R^3$ are replaced by the substituents $R^{12}$ and $R^{13}$, respectively, which, independently of one another, denote hydrogen, straight-chain or branched $C_1$–$C_8$-alkyl, cyclopropyl, cyclopentyl, cyclohexyl, phenyl or benzyl, and where furthermore $R^{12}$ and $R^{13}$ together with the N atom to which they are bonded can form a 5- to 8-membered ring which can contain a further hetero atom from the group consisting of N, O and S.

In a particularly preferred manner, the process according to the invention employs glutacononitriles in which $R^{12}$ and $R^{23}$ are replaced by the substituents $R^{12}$ and $R^{23}$, respectively, which, independently of one another, denote hydrogen, $C_1$–$C_4$-alkyl or benzyl, and where furthermore $R^{22}$ and $R^{23}$ together with the N atom to which they are bonded represent morpholine, pyrrolidine or piperidine, each of which can be substituted by $C_1$–$C_4$-alkyl or by hydroxy-$C_1$–$C_4$-alkyl.

In another preferred manner, $R^5$ and $R^6$ are replaced by the substituents $R^{15}$ and $R^{16}$, respectively, which, independently of one another, denote straight-chain or branched $C_1$–$C_8$-alkyl, cyclopropyl, cyclopentyl, cyclohexyl, benzyl or a 5- to 8-membered saturated or unsaturated ring having 1 or 2 hetero atoms from the group consisting of N, O and S.

In another particularly preferred manner, $R^{15}$ and $R^{16}$ are replaced by the substituents $R^{25}$ and $R^{26}$, respectively, which, independently of one another, denote straight-chain or branched $C_1$–$C_4$-alkyl or benzyl.

The reaction with ammonia gives 2-amino-5-cyano-pyridine, while the reaction with primary a mines or with hydrazincs initially gives 2-imino-5-cyano-1,2-dihydro-pyridine. The 1-methyl derivative of such dihydropyridines is known (J. Chem. Soc. loc. cit.) and is a substance which is stable at room temperature. Under the reaction conditions according to the invention, however, these dihydropyridines undergo a rearrangement reaction to give the aromatic N-substituted 2-amino-5-cyanopyridines. Such a rearrangement reaction is known as Dimroth rearrangement. The reaction of the process according to the invention can be represented for example as follows:

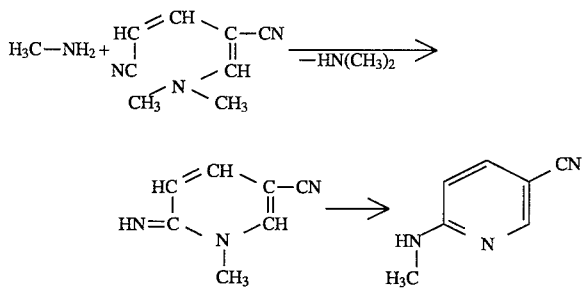

The reaction according to the invention can be carried out in solution or suspension. Suitable reaction media are hydrocarbons, halogenated hydrocarbons, alcohols, water, tertiary amines, ketones, nitriles, dialkyl-carboxamides, N-alkyllactams, peralkyl-ureas, dialkyl sulphoxides, dialkyl sulphones, ethers, peralkylphosphoramidates, or mixtures of several from amongst the above-mentioned groups. According to the invention it is also possible to carry out the process in pure or dilute excess ammonia. Examples of reaction media from the abovementioned groups are: petroleum ether, toluene, xylene, cyclohexane, chlorotoluene, ligroin, 1,2-dichloroethane, triethylamine, acetone, acetonitrile, dimethylacetamide, dimethylformamide, N-methyl-pyrrolidone, N-methyl-caprolactam, tetramethylurea, dimethyl sulphoxide, diethyl sulphone, methyl-tert.-butyl ether, anisole, tetrahydrofuran, methanol, isopropanol and water.

The reaction temperature is from 0° to 200° C., preferably 20° to 150° C. The duration of the reaction according to the invention is a function of the batch size and the nucleophilic properties of the amine and of the temperature and can be between 0.5 and 15 hours.

The molar ratio of nitrogen compound to glutacononitrile is 1 to 100:1, preferably 1 to 10:1. Some or all of the nitrogen compound (III) can also be employed in the form of a salt of an acid, for example in the form of the acetate.

The methylene-glutacononitriles to be employed can be obtained, for example, by reacting glutacononitrile with o-esters. Aminomethylene-glutacononitriles can be obtained in a technically simple procedure by dimerizing suitably substituted β-aminoacrylonitriles.

EXAMPLES

EXAMPLE 1

In a 1.3 l autoclave, 73.5 g of N,N'-dimethylaminomethylene-glutacononitrile, 750 ml of DMF and 136 g of 25% strength aqueous ammonia solution were heated for 2.5 hours at 100° C.

The reaction mixture was concentrated by rotary evaporator, and 60 g of product were obtained as a brown solid. GC analysis (internal standard) allowed a 2-amino-5-cyanopyridine content of 91.7% to be determined, which corresponds to 92.5% of theoretical yield. After recrystallization from water or isopropanol, crystals of melting point 165° C. were obtained.

$^1$H NMR (d-acetone) 6.2–6.6 ppm (s, 2H, NH$_2$), 6.65 ppm (d, 1H, H$^3$), 7.67 ppm (d, 1H, H$^4$), 8.30 ppm (s, 1H, H$^6$).

EXAMPLE 2

15 g of the dinitrile of Example 1 and 7.7 g of ammonium acetate were introduced into an autoclave. 10.6 g of gaseous ammonia were passed in at room temperature, and the autoclave was heated for 2 hours at 100° C. After concentration and aqueous work-up, 2-amino-5-cyano-pyridine was obtained (81.2% of theoretical yield).

EXAMPLE 3

70 g of gaseous ammonia were injected to 15 g of dinitrile of Example 1. After 2 hours at 100° C., the pressure was released, and 12.3 g of product with a purity of 93.6%, which corresponds to 94.8% of theoretical yield, were obtained.

EXAMPLE 4

Analogously to Example 3, 15 g of ethoxymethyleneglutacononitrile were cyclized with ammonia. This gave 2-amino-5-cyanopyridine in a yield of 85% of theory.

EXAMPLE 5

7.4 g of dimethylaminomethylene-glutacononitrile, 100 ml of DMF and 4.4 g of 35.6% strength aqueous methylamine solution were held for 2 hours at 80° C. in an 0.3 l $V_4A$ autoclave. After the mixture had been removed and concentrated, 6.4 g of 2-methylamino-5-cyanopyridine (purity 93%) were obtained, which corresponds to 90.2% of theory.

I claim:

1. A process for the preparation of 6 amino-nicotinonitriles of the formula

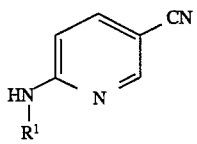

in which $R^1$ denotes hydrogen, straight-chain or branched $C_1$–$C_8$-alkyl, $C_3$–$C_8$-alkenyl, $C_2$–$C_8$-alkoxyalkenyl, $C_3$–$C_8$-cycloalkyl, $C_7$–$C_{10}$-aralkyl or —$N(R^2R^3)$, where $R^2$ and $R^3$ independently of one another denote hydrogen, straight-chain or branched $C_1$–$C_8$-alkyl, phenyl, tolyl, or $C_7$–$C_{10}$-aralkyl or $R^2$ and $R^3$ together with the N atom to which they are bonded from a 5- to 8-membered ring wherein said ring is selected from the group consisting of pyrrolidine, pyrroline, pyrazolidine, imidazolidine, thiazolidine, piperazine, piperidine, morpholine, azepine, or dihydroazacine, wherein a methylene-glutacononitrile of the formula

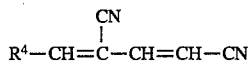

in which $R^4$ represents —$OR^5$ or —$N(R^5,R^6)$ where $R^5$ and $R^6$ independently of $R^1$ and independently of one another have the scope of meaning of $R^1$ with the exception of hydrogen, additionally $R^5$ and $R^6$ together with the N atom to which they are bonded can form a 5- to 6-membered ring wherein said ring is selected from the group consisting of pyrrolidine, piperazine, piperidine, or morpholine, is reacted with a nitrogen compound of the formula

in which $R^1$ has the abovementioned meaning, at a temperature from 0° to 200° C. and where the molar ratio of the nitrogen compound to glutacononitrile is from 1 to 100:1, optionally in the presence of an inert solvent.

2. The process according to claim 1 wherein $R^6$ is replaced by the substituent $R^{14}$, which represents —$N(R^5, R^6)$.

3. The process according to claim 1, wherein $R^1$ is replaced by the substituent $R^{11}$, which represents hydrogen, straight-chain or branched $C_1$–$C_8$-alkyl, cyclopropyl, cyclopentyl, cyclohexyl or benzyl.

4. The process according to claim 3, wherein $R^{11}$ is replaced by the substituent $R^{21}$, which represents hydrogen, straight-chain or branched $C_1$–$C_4$-alkyl or benzyl.

5. The process according to claim 1, wherein $R^2$ and $R^3$ are replaced by the substituents $R^{12}$ and $R^{13}$ respectively, which, independently of one another represent hydrogen, straight-chain or branched $C_1$–$C_8$-alkyl, cyclopropyl, cyclopentyl, cyclohexyl, phenyl or benzyl, where both substitutents $R^{12}$ and $R^{13}$ together with the N atom to which they are bonded form a heterocyclic ring wherein said ring is selected from the group consisting of pyrrolidine, piperazine, piperidine, morpholine.

6. The process according to claim 1, wherein $R^{12}$ and $R^{13}$ are replaced by the substituents $R^{22}$ and $R^{23}$, which independently of one another, represent hydrogen, $C_1$–$C_4$-alkyl, phenyl or benzyl and where furthermore the substituents $R^{22}$ and $R^{23}$ together with the N atom to which they are bonded form morpholine, pyrrolidine or piperidine, each which is optionally substituted by $C_1$–$C_4$-alkyl or by hydroxy-$C_1$–$C_4$-alkyl.

7. The process according to claim 1 wherein $R^5$ and $R^6$ are replaced by the substitutents $R^{15}$ and $R^{16}$ which independently of one another represent straight-chain or branched $C_1$–$C_8$-alkyl, cyclopropyl, cyclopentyl, cyclohexyl, phenyl, benzyl or 5- to 6-membered saturated or unsaturated heterocyclic ring wherein said heterocyclic ring is selected from the group consisting of pyrrolidine, piperazine, piperidine, or morpholine.

8. The process according to claim 7, wherein $R^{13}$ and $R^{16}$ are replaced by the substituents $R^{25}$ and $R^{26}$, respectively, which, independently of one another, represent straight-chain or branched $C_1$–$C_4$-alkyl, phenyl or benzyl.

9. The process according to claim 1, wherein all or some of the nitrogen compound is employed in the form of salt of an acid.

10. The process according to claim 1, wherein the solvent is hydrocarbon, halogenated hydrocarbon, tertiary amine, ketone, nitrile, dialkylcarboxamide, N-alkyl-lactam, peralkylurea, dialkyl sulphoxide, dialkyl sulphone, sulpholane, ether, peralkylphosphoramidate, alcohol, or water.

11. The process according to claim 1, when said solvent is ether, toluene, xylene, cyclohexane, chlorotoluene, ligroin, 1,2-dichloroethane, triethylamine, acetone, acetonitrile, dimethylacetamide, dimethylformamide, N-methylpyrrolidone, N-methyl-caprolactam, tetraethylurea, dimmethyl, sulphoxide, diethyl sulphone, methyl tert.-butyl ether, anisole, tetrahydrofuran, methanol, isopropanol or water.

12. The process according to claim 1, wherein the molar ratio of the nitrogen compound to glutacononitrile is from 1 to 10:1.

13. The process according to claim 1, wherein the temperature is from 20° to 150° C.

* * * * *

UNITED STATES PATENT AND TRADEMARK OFFICE
CERTIFICATE OF CORRECTION

PATENT NO. : 5,480,995
DATED : January 2, 1996
INVENTOR(S) : Kraus, Helmut

It is certified that error appears in the above-indentified patent and that said Letters Patent is hereby corrected as shown below:

Col. 6, line 18    After " peperidine " insert -- or --

Signed and Sealed this

Eleventh Day of June, 1996

Attest:

BRUCE LEHMAN

Attesting Officer        Commissioner of Patents and Trademarks